United States Patent [19]

Cooper et al.

[11] Patent Number: 4,801,598

[45] Date of Patent: Jan. 31, 1989

[54] DIHYDROPYRIDINE ANTI-ALLERGIC AND ANTI-INFLAMMATORY AGENTS

[75] Inventors: Kelvin Cooper; Michael J. Fray; Kenneth Richardson, all of Kent, England

[73] Assignee: Pfizer Inc., New York, N.Y.

[21] Appl. No.: 115,213

[22] Filed: Oct. 30, 1987

[30] Foreign Application Priority Data

Nov. 7, 1986 [GB] United Kingdom ............... 8626698
Apr. 25, 1987 [GB] United Kingdom ............... 8709842

[51] Int. Cl.$^4$ .................... C07D 401/00; A61K 31/44
[52] U.S. Cl. ................................. 514/333; 546/256; 546/271; 514/338
[58] Field of Search ............... 546/256, 271; 514/333, 514/338

[56] References Cited

U.S. PATENT DOCUMENTS 4,707,482 11/1987 Vogel .................. 546/256

FOREIGN PATENT DOCUMENTS 100189 2/1984 European Pat. Off. ............ 546/256

Primary Examiner—John M. Ford
Assistant Examiner—Robert C. Whittenbaugh
Attorney, Agent, or Firm—Peter C. Richardson; J. Trevor Lumb; James M. McManus

[57] ABSTRACT

Compounds of the formula:

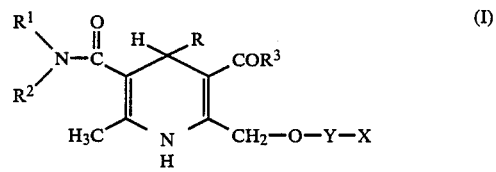

where R is 2-substituted phenyl said substituent being chloro, bromo, cyano, methyl, methylthio, methylsulfonyl, trifluoromethyl, hydroxy, methoxy or benzyloxy; $R^1$ is hydrogen, lower alkyl, pyridyl, thiazolyl, isoxazolyl, thiadiazdyl or thiazdylmethyl; $R^2$ is hydrogen or lower alkyl; $R^3$ is hydroxy, lower alkoxy, benzyloxy, amino, lower alkylamino or morpholino; Y is alkylene having two to six carbon atoms; and X is benzimidazolyl optionally substituted by lower alkyl, chloro or trifluoromethyl.

14 Claims, No Drawings

DIHYDROPYRIDINE ANTI-ALLERGIC AND ANTI-INFLAMMATORY AGENTS

BACKGROUND OF THE INVENTION

This invention relates to dihydropyridines, specifically to certain 4-aryl-5-carbamoyl-1,4-dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-100189.) However the compounds of the present invention are potent and selective antagonists of platelet activating factor and as such they have clinical utility in a quite different area, namely for treating allergic and inflammatory conditions such as asthma and arthritis respectively.

Platelet activating factor (PAF), 1-0-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. For example, in vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute broncho-constriction and chronic inflammatory reactions elicited by allergens in asthma can be mimicked by intratracheal administration of PAF. Accordingly agents with antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock. Intravenous infusion of PAF at doses of 20-200 pmol kg$^{-1}$ min$^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatric patients indicating PAF has a role in the disease of psoriasis. And finally, increasing evidence supports a potential pathophysiological role for PAF in cardiovascular disease. Thus recent studies in angina patients show PAF is released during atrial pacing and in pigs, intracoronary injection of PAF induces a prolonged decrease in coronary flow while in guinea pig hearts it induces regional shunting and ischaemia. The compounds of the invention could thus be of value in the treatment of any of these conditions.

SUMMARY OF THE INVENTION

According to the present invention there are provided compounds of the formula:

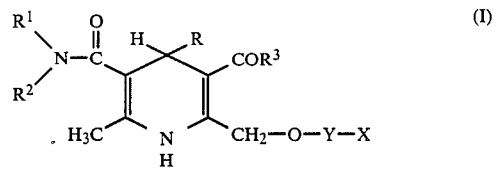

where R is 2-substituted phenyl wherein said substituent is chloro, bromo, cyano, methyl, methylthio, methylsulfonyl, trifluoromethyl, hydroxy, methoxy or benzyloxy; R$^1$ is hydrogen, alkyl of one to four carbon atoms, pyridyl, thiazolyl, cyano, 3-methylisoxazol-5-yl, 2-methyl-1,3,4-thiadiazol-5-yl or thiazol-2-ylmethyl; R$^2$ is hydrogen, or alkyl of one to four carbon atoms; R$^3$ is hydroxy, alkoxy of one to four carbon atoms, benzyloxy, amino, alkylamino of one to four carbon atoms or morpholino; Y is alkylene of two to six carbon atoms having at least two carbon atoms in the chain linking X to the oxygen atom; and X is benzimidazol-1-yl or benzimidazol-2-yl optionally substituted with one or more substituents selected from alkyl of one to four carbon atoms, chloro and trifluoromethyl; and their pharmaceutically acceptable salts.

A preferred group of compounds are those of formula I where R is 2-chlorophenyl, R$^1$ is hydrogen, R$^2$ is t-butyl, R$^3$ is alkoxy of one to four carbon atoms and X is 1-methylbenzimidazol-2-yl. Especially preferred within this group are the compounds where R$^3$ is ethoxy and Y is propylene and where R$^3$ is i-propoxy and Y is propylene.

A second preferred group of compounds of formula I are those where R is 2-chlorophenyl, R$^2$ is hydrogen and R$^3$ is ethoxy. Especially preferred within this group are the compounds where R$^1$ is 2-pyridyl, Y is ethylene and X is 2-methylbenzimidazol-1-yl, where R$^1$ is thiazol2-yl, Y is ethylene and X is 2-methylbenzimidazol-1-yl and where R$^1$ is 2-pyridyl, Y is propylene and X is 1-methylbenzimidazol-2-yl.

A third group of preferred compounds of formula I are those where R is 2-chlorophenyl, R$^1$ is hydrogen, is alkyl of one to four carbon atoms and R$^3$ is alkoxy of one to four carbon atoms. Especially preferred is the compound where R$^2$ is t-butyl, R$^3$ is ethoxy, Y is ethylene and X is 2-methylbenzimidazol-1-yl.

Also considered part of the present invention are methods for treating an allergic or inflammatory condition in a mammal which comprises administering to said mammal an anti-allergic or antiinflammatory effective amount of a compound of formula I. In addition the present invention comprises a pharmaceutical composition comprising an anti-allergic or antiinflammatory effective amount of a compound of formula I and a pharmaceutically acceptable carrier of diluent.

The compounds of the formula (I) contain at least one asymmetric centre and exist as one or more pairs of enantiomers. Such pairs or individual isomers may be separable by physical methods, e.g. by fractional crystallisation or chromatography of the parent compounds or of a suitable salt or derivatives thereof. The invention includes all the enantiomers whether separated or not.

The pharmaceutically acceptable acid addition salts of the compounds of the formula (I) which form such salts are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, tartrate, methanesulphonate, benzenesulphonate and p-toluenesulphonate salts.

DETAILED DESCRIPTION OF THE INVENTION

The compounds of formula I may be obtained by the Hantzsch synthesis, according to the following reaction scheme:

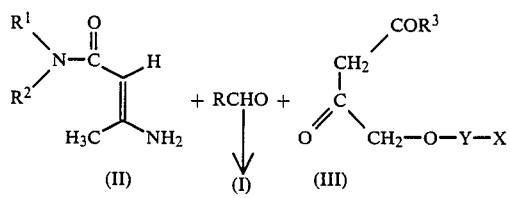

wherein R, $R^1$, $R^2$, $R^3$, Y and X are as previously defined.

In a typical procedure, the ketoester (III) and aldehyde are heated under reflux in a suitable organic solvent, e.g. a $C_1$-$C_4$ alkanol such as ethanol, for about 15 minutes, and then the aminocrotonamide (II) is added. Alternatively the aminocrotonamide (II), the ketoester (III) and the aldehyde can be heated together in the solvent. Optionally a small amount of a lower alkanoic acid such as acetic acid is added to neutralise the solution. The resulting solution can then be heated at 60°-130° C., preferably under reflux, until the reaction is essentially complete, typically in 24 hours or less. The product of the formula (I) can then be isolated and purified by conventional procedures, for example by partition, recrystallisation or by chromatography.

Certain compounds of formula (I) are also conveniently obtained by means of simple chemical transformation reactions. Thus for example compounds of formula (I) wherein $R^3$ is benzyloxy may be subjected to a conventional catalytic hydrogenation to yield the corresponding compounds wherein $R^3$ is OH. The acid product may then be reacted with ammonia or with an amine in the presence of a diimide coupling agent, to yield the amide or substituted amide wherein $R^3$ is $NR^4R^5$. Appropriate reagents and conditions for these transformations will be well known to those skilled in the art.

The ketoesters (III) are either known compounds or can be prepared by methods analogous to those of the prior art, such as the method described in European Pat. No. 100189 which is essentially the method of Troostwijk and Kellogg, J.C.S. Chem. Comm., 1977, page 932, or as described in the Preparations given hereafter. Similarly the amino-crotonamides (II) are either known compounds or can be prepared by conventional procedures, for example from the ketoamide by reaction with ammonia. Also the aldehydes RCHO are either known or can be prepared by known methods in accordance with literature precedents.

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated with stirring for two minutes at 37° C. in a Paton aggregometer, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection or administered orally be gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the PAF challenge repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2-1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use in medicine, in particular in the treatment of allergic and inflammatory conditions in a human being.

The preparation of the compounds of the invention is further illustrated by the following Examples.

EXAMPLE 1

5-(N-t-Butylcarbamoyl)-4-(2-chlorophenyl)-3-ethoxycarbonyl-6-methyl-2-[2-(2-methylbenzimidazol-1-yl)ethoxymethyl]-1,4-dihydropyridine (a) Ethyl 4-[2-(2-methylbenzimidazol-1-yl)ethoxy]-3-ketobutanoate Sodium hydride (1.46 g, 80% suspension in oil) was suspended in dry tetrahydrofuran (60 ml) under nitrogen. 2-Methylbenzimidazol-1-ylethanol (4.3 g) was added and the suspension was sonicated at 40° C. for 2 hours. Ethyl 4-chloroacetoacetate (4.02 g) in tetrahydrofuran (20 ml) was added dropwise and sonication continued for a further 6 hours. The reaction was poured into 1N hydrochloric acid (50 ml), the tetrahydrofuran was removed under reduced pressure and the aqueous phase washed with toluene. The aqueous phase was adjusted to pH7 with potassium carbonate and extracted with dichloromethane (2×100 ml). The organic extracts were combined, dried over magnesium sulphate and the solvent removed under reduced pressure. The residue was chromatographed on silica eluting with 5% methanol in ethyl acetate. The fractions containing the product were combined and evaporated to yield the title compound (4.4 g, 59%) as a red oil.

NMR (CDCl$_3$): 1.27 (t, J=6 Hz, 3H); 2.66 (s, 3H); 3.34 (s, 2H); 3.85 (t, J=4 Hz, 2H); 4.08 (s, 2H); 4.13 (q, J=6 Hz, 2H); 4.36 (t, J=4 Hz, 2H); 7.30 (m, 3H); 7.70 (m, 1H).

(b) 5-(N-t-Butylcarbamoyl)-4-(2-chlorophenyl)-3-ethoxycarbonyl-6-methyl-2-[2-(2-methylbenzimidazol-1-yl)ethoxymethyl]-1,4-dihydropyridine N-t-butyl-3-ketobutanamide (0.29 g) was dissolved in saturated ethanolic ammonia (15 ml) and stirred overnight at room temperature. The solution was evaporated to yield N-t-butyl-3-aminocrotonamide which was used directly. The crude residue was dissolved in ethanol (8 ml), 2-chlorobenzaldehyde (0.28 g) and ethyl 4-[2-(2-methylbenzimidazol-1-yl)ethoxy]-3-ketobutanoate (0.61 g) were added. The mixture was heated at reflux overnight, cooled and the solvent removed under reduced pressure. The residue was chromatographed on silica eluting with 4% diethylamine in ethyl acetate. The fractions containing the product were combined and evaporated. The residue was re-chromatographed on silica eluting with 5% methanol in ethyl acetate. The fractions containing the product were combined and evaporated to yield the title compound (0.17 g, 15%). m.p. 157°-161° C. Found: C, 65.66; H, 6.68; N, 9.74. $C_{31}H_{37}ClN_4O_4$ requires C, 65.89; H, 6.60; N, 9.91%.

EXAMPLES 2-7

The following compounds were prepared by the method of Example 1 using as starting materials the appropriate N-substituted 3-ketobutanamide, 2-chlorobenzaldehyde and ethyl 4-[2-(2-methylbenzimidazol-1-yl)ethoxy]-3-ketobutanoate.

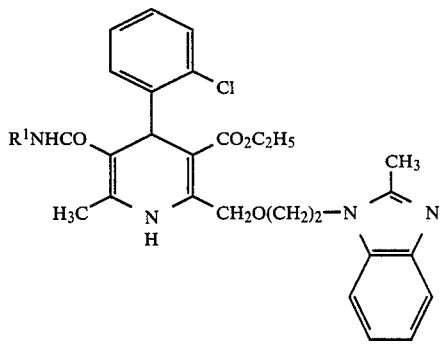

| Example No. | R$^1$ | m.p. °C. | Analysis % (Theoretical in brackets) | | |
|---|---|---|---|---|---|
| | | | C | H | N |
| 2 | (pyridin-2-yl-methyl) | 185-189 | 65.20 (65.58 | 5.54 5.47 | 11.72 11.96) |
| 3 | (thiazol-2-yl) | 211-213 | 60.81 (60.86 | 5.26 5.07 | 11.70 11.83) |
| 4 | (3-methylisoxazol-5-yl) | 207-208 | 62.02 (62.16 | 5.39 5.51 | 11.47 11.70)[1] |
| 5 | (3-methyl-1,2,4-thiadiazol-5-yl) | 194-196 | 58.49 (58.49 | 4.99 5.20 | 13.57 13.65)[1] |
| 6 | (thiazol-2-yl-methyl) | 132-139 | 59.96 (59.66 | 5.34 5.49 | 11.46 11.22)[2] |
| 7 | NC— | 140-147 | 61.55 | 5.33 | 12.86 |

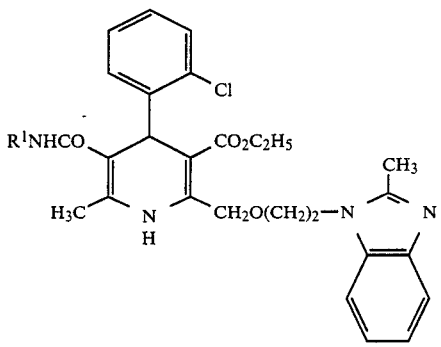

| Example No. | R¹ | m.p. °C | C | H | N |
|---|---|---|---|---|---|
| | | | (61.42 | 5.43 | 12.79)³ |

[1] Hemihydrate;
[2] Hydrate;
[3] 0.75 Hydrate.

EXAMPLES 8–13

The following compounds were prepared by the method of Example 1(b) using as starting materials N-t-butyl-3-aminocrotonamide, ethyl 4-[2-(2-methylbenzimidazol-1-yl)ethoxy]-3-ketobutanoate and the appropirate substituted-benzaldehyde:

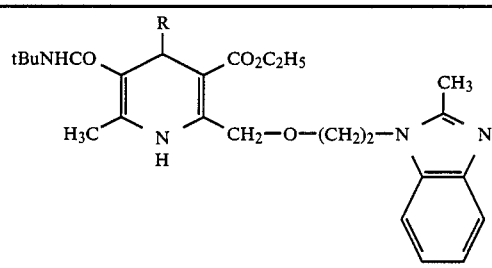

| Example No. | R | m.p. °C | C | H | N |
|---|---|---|---|---|---|
| 8 | (o-CN-phenyl) | 204–208 | 68.74 (69.17 | 6.96 6.71 | 12.37 12.60) |
| 9 | (o-Br-phenyl) | 173–174 | 61.06 (61.08 | 6.17 6.12 | 9.14 9.19) |
| 10 | (o-SO₂CH₃-phenyl) | 204–210 | 62.82 (63.14 | 6.98 6.62 | 8.93 9.20) |
| 11 | (o-SCH₃-phenyl) | 65–70 | 66.26 (66.64 | 7.34 6.99 | 9.73 9.71) |

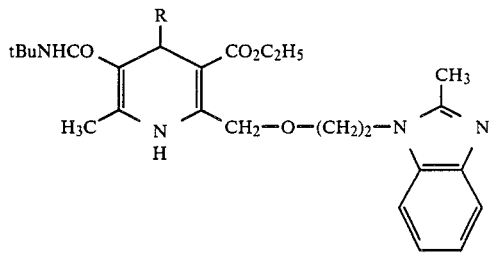

| Example No. | R | m.p. °C | C | H | N |
|---|---|---|---|---|---|
| 12 | (o-OCH₂C₆H₅-phenyl) | 72–75 | 70.91 (70.59 | 7.07 6.97 | 9.05 8.67) |
| 13 | (o-OH-phenyl) | 171–173 | 67.65 (68.10 | 7.14 7.01 | 10.02 10.25) |

EXAMPLES 14–16

The following compounds were prepared by the method of Example 1(b) using as starting materials N-t-butyl 3-aminocrotonamide, 2-chlorobenzaldehyde and the appropriate ester of 4-[2-(2-methylbenzimidazol-1-yl)ethoxy]-3-ketobutanoate:

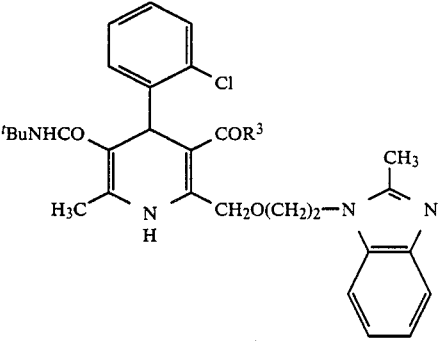

| Example No. | R³ | m.p. °C | C | H | N |
|---|---|---|---|---|---|
| 14 | OC(CH₃)₃ | 187–188 | 66.70 (66.82 | 6.89 6.97 | 9.36 9.45) |
| 15 | OCH(CH₃)₂ | 110–116 | 66.27 (66.37 | 6.87 6.79 | 9.51 9.67) |
| 16 | OCH₂C₆H₅ | 158–160 | 67.96 (67.97 | 6.49 6.39 | 8.80 8.94)¹ |

[1] Hemihydrate.

EXAMPLE 17

5-(N-t-Butylcarbamoyl)-3-carboxy-4-(2-chlorophenyl)-6-methyl-2-[2-(2-methylbenzimidazol-1-yl)ethoxymethyl]-1,4-dihydropyridine Palladium on carbon (0.10 g; 5%) was added to a solution of 3-benzyloxycarbonyl-5-(N-t-butylcarbamoyl)-4-(2-chlorophenyl)-6-methyl-2-[2-(2-methylbenzimidazol-1-yl)ethoxymethyl]-1,4-dihydropyridine (0.143 g, 0.23 mmol) in ethanol (8 ml) and the mixture stirred under hydrogen (1 bar) at 28° C. for 5 hours. The catalyst was removed by filtration, the solvent evaporated and the residue triturated with hot diethyl ether to yield the title product as a white solid (0.097 g, 79%), m.p. 187°–188° C. Found: C,62.77; H, 6.35; N, 10.09. $C_{29}H_{33}ClN_4 \cdot H_2O$ requires C, 63.17; H, 5.96; N, 10.09%.

EXAMPLE 18

5-(N-t-Butylcarbamoyl)-4-(2-chlorophenyl)-3-(N-isopropylcarbamoyl)-6-methyl-2-[2-(2-methylbenzimidazol-1-yl)ethoxymethyl]-1,4-dihydropyridine Dimethylaminopyridine (0.026 g, 0.21 mmol) and N,N'-dicyclohexylcarbodiimide (0.048 g, 0.23 mmol) were added to a stirred suspension of 5-(N-t-butylcarbamoyl)-3-carboxy-4-(2-chlorophenyl)-6-methyl-2-[2-(2-methylbenzimidazol-1-yl)ethoxymethyl]-1,4-dihydropyridine (0.107 g, 0.2 mmol) in dry dichloromethane (2 ml). The mixture was stirred for 16 hours at 24° C. and then treated with isopropylamine (0.17 ml, 2 mmol). The mixture was stirred for a further 3 hours and the solvent then evaporated and the residue chromatographed on silica gel, eluting with a mixture of methanol and ethyl acetate (1:9) to afford the title compound as a colourless oil which crystallised on standing (0.08 g, 68%), m.p. 191–193° C. Found: C, 66.18; H, 7.38; N, 11.72. $C_{32}H_{40}ClN_5O_3$ requires: C, 66.48; H, 6.97; N, 12.11%.

EXAMPLES 19–20

The following compounds were prepared by the method of Example 18, but using ammonia or morpholine respectively instead of isopropylamine.

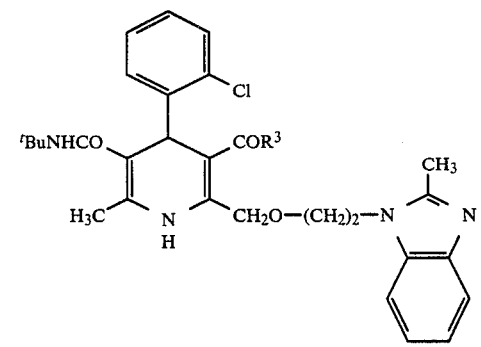

| Example No. | $R^3$ | m.p. °C. | Analysis % (Theoretical in brackets) | | |
|---|---|---|---|---|---|
| | | | C | H | N |
| 19 | —NH₂ | 161–163 | 63.89 (63.49 | 6.47 6.23 | 12.85 12.50) |

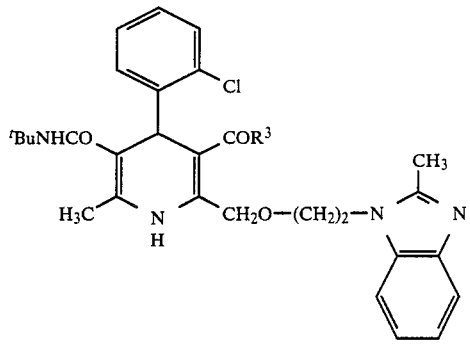

| Example No. | $R^3$ | m.p. °C. | Analysis % (Theoretical in brackets) | | |
|---|---|---|---|---|---|
| | | | C | H | N |
| 20 | —N⌒O | foam <30° C. | 65.72 (65.39 | 7.01 6.65 | 11.15 11.55) |

EXAMPLE 21

5-(N-t-Butylcarbamoyl-4-(2-chlorophenyl)-3-ethoxycarbonyl-6-methyl-2-[3-(1-methylbenzimidazol-2-yl)propoxymethyl]-1,4-dihydropyridine (a) 3-(1-Methylbenzimidazol-2-yl)propan-1-ol N-Methyl-ortho-phenylenediamine dihydrochloride (4.88 g), and butyrolactone (3.22 g) were stirred at reflux for 18 hours in 4N hydrochloric acid (25 ml). The reaction mixture was cooled, the pH adjusted to 8 with concentrated aqueous ammonia and filtered. The solid was recrystallised from ethyl acetate to yield the title compound as a white solid (3.39 g 71%), m.p. 107° C. Found: C, 69.22; H, 7.38; N, 14.73. $C_{11}H_{14}N_2O$ requires C, 69.45; H, 7.42; N, 14.72%.

(b) Ethyl 4-[3-(1-methylbenzimidazol-2-yl)propoxy]-3-keto butanoate

Sodium hydride (1.7 g, 60% suspension in oil) was suspended in dry tetrahydrofuran (50 ml) under nitrogen. 3-(1-Methylbenzimidazol-2-yl)propan-1-ol (3.30 g) was added and the suspension was sonicated at room temperature for ½ hour. Ethyl-4-chloroacetoacetate (2.85 g) in dry tetrahydrofuran (10 ml) was added dropwise and sonication continued at up to 40° C. for a further 3 hours. The reaction mixture was poured into 1N hydrochloric acid (50 ml) and the tetrahydrofuran removed under reduced pressure. The aqueous solution was washed with toluene (100 ml), the pH adjusted to 7 with aqueous potassium carbonate and extracted with dichloromethane (2×100 ml). The organic extracts were combined, dried over magnesium sulphate and the solvent removed under reduced pressure. The residue was chromatographed on silica eluting with 10% methanol in ethyl acetate. The fractions containing the product were combined and evaporated yielding the title compound (3.61 g, 65%) as a red oil.

N.M.R. (CDCl₃): 1.28 (t, J=6 Hz,3H); 2.25 (m, 2H); 3.03 (t, J=6 Hz, 2H); 3.50 (s, 2H); 3.67 (t, J=6 Hz, 2H); 3.79 (s, 3H); 4.16 (s, 2H); 4.20 (q, J=6 Hz, 2H); 7.27 (m, 3H); 7.71 (m, 1H).

(c)

5-(N-t-Butylcarbamoyl)-4-(2-chlorophenyl)-3-ethoxycarbonyl-6-methyl-2-[3-(1-methylbenzimidazol-2-yl)propoxymethyl]-1,4-dihydropyridine N-t-Butyl-3-aminocrotonamide (0.63 g), 2-chlorobenzaldehyde (0.56 g) and ethyl 4-[3-(1-methylbenzimidazol-2-yl)propoxy]-3-ketobutanoate (1.27 g) were dissolved in ethanol (16 ml) and stirred under reflux for 15 hours. The reaction mixture was cooled and the solvent removed under reduced pressure. The residue was chromatographed on silica eluting with 3% methanol in ethyl acetate. The fractions containing the product were combined and evaporated. Recrystallisation of the resulting foam from ethanol yielded the title compound as a white solid (0.33 g, 14%), m.p. 202° C. Found: C, 66.17; H, 6.92; N, 9.48. $C_{32}H_{39}ClN_4O_4$ requires C, 66.36; H, 6.79; N, 9.68%.

EXAMPLE 22

5-(N-t-Butylcarbamoyl)-4-(2-chlorophenyl)-3-isopropoxycarbonyl-6-methyl-2-[3-(1-methylbenzimidazol-2-yl)-propoxymethyl]-1,4-dihydropyridine The procedure of Example 21(c) was followed using isopropyl 4-[3-(1-methylbenzimidazol-2-yl)propoxy]-3-ketobutanoate, 2-chlorobenzaldehyde and N-t-butyl-3-aminocrotonamide as starting materials to yield the title compound as a white solid m.p. 216° C. Found: C, 66.62; H, 6.78; N, 9.35. $C_{33}H_{41}ClN_4O_4$ requires C, 66.82; H, 6.97; N, 9.45%.

EXAMPLES 23-31

The following compounds were prepared by the method of Example 1(b) or Example 21(c) using as starting materials N-pyrid-2-yl-3-aminocrotonamide or N-t-butyl-3-aminocrotonamide, 2-chlorobenzaldehyde and the appropriate 3-ketobutanoate.

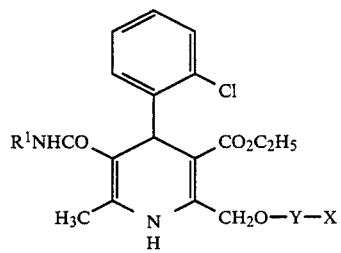

| Example No. | R¹ | Y—X | m.p. °C. | Analysis % (Theoretical in Brackets) | | |
|---|---|---|---|---|---|---|
| | | | | C | H | N |
| 23 | pyrid-2-yl | —(CH₂)₂—N(CH₃)=N- (5,6-dichlorobenzimidazol-2-yl, 1-methyl) | 185-190 | 58.87 (58.68 | 4.67 4.62 | 10.57 10.69) |
| 24 | pyrid-2-yl | —(CH₂)₂—N=CH—N- (benzimidazol-2-yl) | 152-153 | 65.26 (65.09 | 5.61 5.25 | 12.13 12.25) |
| 25 | pyrid-2-yl | —(CH₂)₂—N(CH₃)=N- (5,6-dimethylbenzimidazol-2-yl, 1-methyl) | 198-199 | 66.23 (66.50 | 5.91 5.87 | 11.34 11.41) |

-continued
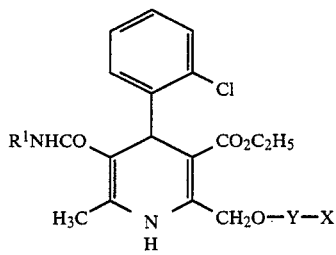
| Example No. | R¹ | Y—X | m.p. °C. | C | H | N |
|---|---|---|---|---|---|---|
| 26 | 2-pyridyl | —CH₂C(CH₃)₂—N(2-methylbenzimidazol-1-yl) | 166–168 | 66.23 (66.50 | 6.07 5.87 | 11.28 11.41) |
| 27 | 2-pyridyl | —(CH₂)₂—N(2-ethylbenzimidazol-1-yl) | 155 | 66.09 (66.05 | 5.48 5.71 | 11.64 11.67) |
| 28 | (CH₃)₃C— | —(CH₂)₂—N(2-ethylbenzimidazol-1-yl) | 183 | 65.50 (65.35 | 6.91 6.86 | 9.18 9.53)[1] |
| 29 | 2-pyridyl | —(CH₂)₂—N(2-trifluoromethylbenzimidazol-1-yl) | 113 | 60.26 (60.05 | 4.48 4.37 | 11.01 10.94) |
| 30 | (CH₃)₃C— | —(CH₂)₂—N(2-trifluoromethylbenzimidazol-1-yl) | 113 | 60.01 (60.14 | 5.61 5.54 | 8.98 9.05) |
| 31 | 2-pyridyl | —(CH₂)₃—(1-methylbenzimidazol-2-yl) | 177 | 63.98 (63.87 | 5.68 5.51 | 10.56 10.64)[2] |
[1] Hemihydrate
[2] Hemifumarate.

PREPARATION 1

2,5,6-Trimethylbenzimidazol-1-ylethanol (a) 2,5,6-Trimethylbenzimidazole (9.4 g) and sodium hydride (2.1 g, 80% suspension in oil) were sonicated in dry tetrahydrofuran (150 ml) for 1 hour. Ethyl 2-bromoacetate (9.8 g) in dry tetrahydrofuran (50 ml) was added and the reaction sonicated at 40° C. for 2 hours. The reaction was partitioned between ethyl acetate (300 ml) and water (100 ml), the organic phase dried over magnesium sulphate and the solvent removed under reduced pressure to yield ethyl 2-(2,5,6-trimethylbenzimidazol-1-yl)acetate (13.5 g).

(b) A solution of ethyl 2-(2,5,6-trimethylbenzimidazol-1-yl)acetate (6.15 g) in dry tetrahydrofuran (20 ml) was added to a suspension of lithium aluminium hydride (0.95 g) was dry tetrahydrofuran (60 ml) at 0° C. The reaction was allowed to warm to room temperature and stirred at room temperature for 1 hour. Water (1 ml) was added dropwise to the reaction followed by 15% sodium hydroxide (3 ml) and water (3 ml). The suspension was filtered and the solvent removed under reduced pressure. The product was dissolved in dichloromethane, dried over magnesium sulphate and the solvent removed under reduced pressure. The residue was triturated with acetone, the solid filtered and dried under reduced pressure to yield the title compound (1.9 g, 37%), m.p. 191°-2° C. Found: C, 70.17; H, 8.07; N, 13.56. $C_{12}H_{16}N_2O$ requires: C, 70.59; H, 7.84; N, 13.72%.

PREPARATION 2

2-Methyl-2-(2-methylbenzimidazol-1-yl)propan-1-ol (a) N-(1-Hydroxy-2-methylprop-2-yl)-2-nitroaniline (10 g) in ethanol (200 ml) was hydrogenated over 5% palladium on charcoal (0.5 g) at 50 p.s.i. for 2 hours. The reaction was filtered and the solvent removed under vacuum to yield N-(1-hydroxy-2-methylprop-2-yl)benzene 1,2-diamine (8.4 g, 98%).

| Preparation No. | Y—X | NMR (CDCl₃) |
|---|---|---|
| 4 | 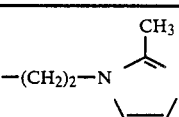 | 1.27 (t, J = 6Hz, 3H); 2.65 (s, 3H); 3.36 (s, 2H); 3.85 (t, J = 4Hz, 2H); 4.13 (s, 2H); 4.15 (q, J = 6Hz, 2H); 4.33 (t, J = 4Hz, 2H); 7.44 (s, 1H); 7.77 (s, 1H). |
| 5 | 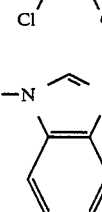 | 1.27 (t, J = 6Hz, 3H); 3.40 (s, 2H); 3.89 (t, J = 4Hz, 2H); 4.13 (s, 2H); 4.16 (q, J = 6Hz, 2H); 4.43 (t, J = 4Hz, 2H); 7.32 (m, 2H); 7.42 (m, 1H); 7.85 (m, 1H); 8.01 (s, 1H). |
| 6 | 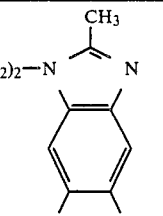 | 1.27 (t, J = 6Hz, 3H); 2.38 (s, 3H); 2.42 (s, 3H); 2.63 (s, 3H); 3.37 (s, 2H); 3.86 (t, J = 6Hz, 2H); 4.08 (s, 2H); 4.16 (q, J = 6Hz, 2H), 4.32 (t, J = 6Hz, 2H); 7.09 (s, 1H); 7.46 (s, 1H). |
| 7 | 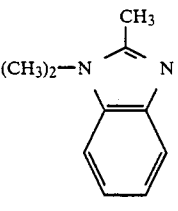 | 1.26 (t, J = 6Hz, 3H); 1.93 (s, 6H); 2.83 (s, 3H); 3.30 (s, 2H); 3.97 (s, 2H); 4.03 (s, 2H), 4.15 (q, J = 6Hz, 2H); 7.20 (m, 2H); 7.56 (m, 1H); 7.70 (m, 1H). |
| 8 | 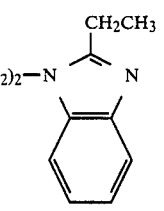 | 1.26 (t, J = 6Hz, 3H); 1.50 (t, J = 6Hz, 3H); 2.96 (q, J = 6Hz, 2H); 3.35 (s, 2H); 3.86 (t, J = 4Hz, 2H); 4.09 (s, 2H); 4.15 (q, J = 4Hz, 2H); 4.38 (t, J = 4Hz, 2H); 7.24–7.34 (m, 3H); 7.75 (m, 1H). |
| 9 | 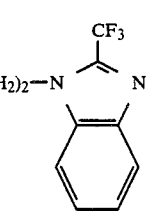 | 1.25 (t, J = 6Hz, 3H); 3.35 (s, 2H); 3.92 (t, J = 4Hz, 2H); 4.11 (s, 2H); 4.12 (q, J = 6Hz, 2H); 4.59 (t, J = 4Hz, 2H); 7.43 (m, 2H); 7.60 (d, J = 6Hz, 1H); 7.88 (d, J = 6Hz, 1H). |

PREPARATION 10

Benzyloxy 4-[2-(2-methylbenzimidazol-1-yl)ethoxy]-3-ketobutanoate

A solution of ethyl 4-[2-(2-methylbenzimidazol-1-yl)ethoxy]-3-ketobutanoate (0.601 g, 2 mmol) and benzylalcohol (0.83 ml, 8 mmol) in toluene (8 ml) was heated under reflux for 18 hours. The solvent was evaporated and the residue chromatographed on silica gel, eluting with ethyl acetate followed by 10% methanol in ethyl acetate to afford the benzyl ester as a red oil (0.49 g, 65%).

PREPARATION 11

Isopropyl 4-[3-(1-methylbenzimidazol-2-yl)propoxy]-3-ketobutanoate

Ethyl 4-[3-(1-methylbenzimidazol-2-yl)propoxy]-3-keto butanoate (1.1 g) was stirred in isopropyl alcohol (80 ml) at reflux for 48 hours. The solvent was removed under reduced pressure and the residue chromatographed on silica eluting with 6% methanol in ethyl acetate to yield the title compound as a red oil (0.75 g, 65%).

We claim:

1. A compound of the formula

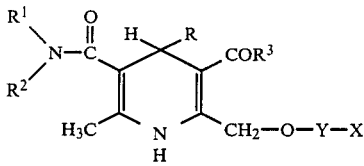

or a pharmaceutically acceptable salt thereof, wherein R is 2-substituted phenyl wherein said substituent is chloro, bromo, cyano, methyl, methylthio, methylsulfonyl, trifluoromethyl, hydroxy, methoxy or benzyloxy; $R^1$ is hydrogen, alkyl having one to four carbon atoms, pyridyl, thiazolyl, cyano, 3-methylisoxazol-5-yl, 2-methyl-1,3,4-thiadiazol-5-yl or thiazol-2-ylmethyl; $R^2$ is hydrogen or alkyl having one to four carbon atoms; $R^3$ is hydroxy, alkoxy having one to four carbon atoms, benzyloxy, amino or alkylamino having one to four carbon atoms; Y is alkylene having two to six carbon atoms having at least two carbon atoms in the chain linking X to the oxygen atom; and X is benzimidazol-1-yl or benzimidazol-2-yl optionally substituted with one or more substituents selected from alkyl having one to four carbon atoms, chloro and trifluoromethyl.

2. A compound of claim 1, wherein R is 2-chlorophenyl, $R^1$ is hydrogen, $R^2$ is t-butyl, $R^3$ is alkoxy having one to four carbon atoms and X is 1-methylbenzimidazol-2-yl.

3. The compound of claim 2, wherein $R^3$ is ethoxy and Y is propylene.

4. The compound of claim 2, wherein $R^3$ is i-propoxy and Y is propylene.

5. A compound of claim 1, wherein R is 2-chlorophenyl, $R^2$ is hydrogen and $R^3$ is ethoxy.

6. The compound of claim 5, wherein $R^1$ is 2-pyridyl, Y is ethylene and X is 2-methylbenzimidazol-1-yl.

7. The compound of claim 5, wherein $R^1$ is thiazol-2-yl, Y is ethylene and X is 2-methylbenzimidazol-1-yl.

8. The compound of claim 5, wherein $R^1$ is 2-pyridyl, Y is propylene and X is 1-methylbenzimidazol-2-yl.

9. The compound of claim 1, wherein R is 2-chlorophenyl, $R^1$ is hydrogen, $R^2$ is alkyl having one to four carbon atoms and $R^3$ is alkoxy having one to four carbon atoms.

10. The compound of claim 9, wherein $R^2$ is t-butyl, $R^3$ is ethoxy, Y is ethylene and X is 2-methylbenzimidazol-1-yl.

11. A method of treating an allergic condition in a mammal which comprises administering to said mammal an anti-allergic effective amount of a compound according to claim 1.

12. A method of treating an inflammatory condition in a mammal which comprises administering to said mammal an antiinflammatory effective amount of a compound according to claim 1.

13. A pharmaceutical composition comprising an anti-allergic effective amount of a compound according to claim 1 and a pharmaceutically acceptable carrier or diluent.

14. A pharmaceutical composition comprising an antiinflammatory effective amount of a compound according to claim 1 and a pharmaceutically acceptable carrier or diluent.

* * * * *